(12) United States Patent
Holbrooks et al.

(10) Patent No.: US 12,708,404 B2
(45) Date of Patent: Aug. 18, 2026

(54) UTERINE MANIPULATOR

(71) Applicant: Conmed Corporation, Largo, FL (US)

(72) Inventors: Ashley Holbrooks, New Hartford, NY (US); Rachelle D. Fitzgerald, Massapequa, NY (US); Christopher Yantsides, Whitesboro, NY (US); David Hughes, Rome, NY (US); Xiao Wu, North Chili, NY (US); Irtiza Ali, New Haven, CT (US)

(73) Assignee: Conmed Corporation, Largo, FL (US)

( * ) Notice: Subject to any disclaimer, the term of this patent is extended or adjusted under 35 U.S.C. 154(b) by 58 days.

(21) Appl. No.: 19/004,582

(22) Filed: Dec. 30, 2024

(65) Prior Publication Data

US 2025/0318856 A1 Oct. 16, 2025

Related U.S. Application Data

(63) Continuation of application No. 17/699,787, filed on Mar. 21, 2022, now Pat. No. 12,178,474, which is a continuation of application No. 17/198,506, filed on Mar. 11, 2021, now Pat. No. 11,877,772, which is a continuation of application No. 15/617,299, filed on Jun. 8, 2017, now Pat. No. 11,278,322.

(60) Provisional application No. 62/347,781, filed on Jun. 9, 2016.

(51) Int. Cl.
*A61B 17/42* (2006.01)
*A61B 17/00* (2006.01)
*A61B 17/02* (2006.01)
*A61M 5/00* (2006.01)
*A61M 25/10* (2013.01)

(52) U.S. Cl.
CPC .... *A61B 17/4241* (2013.01); *A61B 17/00234* (2013.01); *A61B 17/0218* (2013.01); *A61B 17/42* (2013.01); *A61M 5/007* (2013.01); *A61M 25/10185* (2013.11); *A61B 2017/00557* (2013.01)

(58) Field of Classification Search
CPC .......... A61B 17/4241; A61B 17/00234; A61B 17/42; A61M 29/00; A61M 2210/14–1491
See application file for complete search history.

(56) References Cited

U.S. PATENT DOCUMENTS

2016/0270819 A1* 9/2016 Ahluwalia ......... A61B 17/4241
2018/0221630 A1* 8/2018 Obradovic ........ A61M 25/1018

* cited by examiner

*Primary Examiner* — Brigid K Byrd
(74) *Attorney, Agent, or Firm* — Bond, Schoeneck & King, PLLC; Frederick J.M. Price

(57) ABSTRACT

A uterine manipulator device includes: an elongated cannulated tube comprising a proximal end and a distal end; a cervical cup having a top proximal portion of a first diameter and a base distal portion of a second smaller diameter, wherein: the base distal portion includes a hole formed therein having a perimeter including a distal end and a proximal end, and including a longitudinal axis positioned therethrough; one of the proximal end of the perimeter and the distal end of the perimeter is angled away from the longitudinal axis and the other of the proximal end of the perimeter and the distal end of the perimeter is in line with the longitudinal axis; and the elongated cannulated tube is positioned through the hole in the cervical cup.

18 Claims, 7 Drawing Sheets

UTERINE MANIPULATOR

CROSS-REFERENCE TO RELATED APPLICATIONS

The present application is a continuation of U.S. Non-Provisional patent application Ser. No. 17/699,787 filed Mar. 21, 2022, which is a continuation of U.S. Non-Provisional patent application Ser. No. 17/198,506 filed Mar. 11, 2021 which is a continuation of U.S. Non-Provisional patent application Ser. No. 15/617,299 filed on Jun. 8, 2017 (now U.S. Pat. No. 11,278,322), which claims priority to and the benefit of U.S. Provisional Patent Application No. 62/347,781, filed on Jun. 9, 2016, the entire contents of which are hereby incorporated by reference.

FIELD OF THE INVENTION

The present disclosure relates generally to devices and methods for manipulation of the uterus and cervix in surgical and diagnostic procedures.

BACKGROUND

Various conventional forms of uterine manipulators and vaginal cervical retractors are known. For example, U.S. Pat. No. 5,209,754 describes a vaginal cervical retractor generally consisting of a proximal (to the patient) half-length curved outer shaft (corresponding to the curve of the posterior pelvis) and a straight distal half connected to a handle, an inner cap positioned within an outer cap and a circular disc located at the proximal end of the outer tube, and an inner plastic tube positioned through the outer tube and the circular disc, inner cap and outer cap (which can include one cervical cup in certain conventional devices) with a balloon on the proximal end. The vaginal cervical retractor is used to maneuver and visualize the uterus during various medical examinations and laparoscopic procedures while maintaining pneumoperitoneum. Such examinations and procedures include a complete, total laparoscopic hysterectomy, a partial laparoscopic hysterectomy, and a colpotomy. While the vaginal cervical retractor maneuvers the uterus during a complete, total laparoscopic hysterectomy, for example, by, in part, positioning and inflating the balloon within the uterine cavity, capturing the vaginal fornix in the inner cap, and maintaining the pneumoperitoneum by properly positioning the disc, a laparoscope can be inserted through a surgically formed incision in the wall of the patient's abdomen to allow for visualization of the peritoneal cavity and the uterus to assist with the hysterectomy. Other conventional forms of uterine manipulators and vaginal cervical retractors exist and contain similar features.

However, some conventional uterine manipulators and vaginal cervical retractors do not include a mechanism or structural configuration to sufficiently maintain the cervical cup on the inner or manipulator tube during a particular medical procedure (as described above). Additionally, some conventional uterine manipulators and vaginal cervical retractors do not include a configuration to sufficiently fit and retain the balloon on the proximal end of the inner or manipulator tube. Indeed, the balloon of such conventional uterine manipulators and vaginal cervical retractors often bunches up during assembly implicating certain potential safety concerns during the particular medical procedure.

Accordingly, there is a need in the art for improved devices and methods for manipulation of the uterus and cervix in surgical and diagnostic procedures including a mechanism or structural configuration to sufficiently maintain the cervical cup on the inner or manipulator tube, and a structural configuration to sufficiently fit and retain the balloon on the proximal end of the inner or manipulator tube.

Description of the Related Art Section Disclaimer: To the extent that specific patents/publications/products are discussed above in this Background Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Background Section and/or throughout the application, the descriptions/disclosures of which are all hereby incorporated by reference into this document in their respective entirety(ies).

SUMMARY OF THE INVENTION

The present disclosure is directed to inventive devices and methods for manipulation of the uterus and cervix in surgical and diagnostic procedures. Various embodiments and implementations herein are directed to a uterine manipulator device that includes a manipulator tube and a cervical cup with a hole feature (preferably centralized) positioned at the base of the cervical cup through which the manipulator tube is positioned. The distal portion of the perimeter of the hole feature can be (but does not need to be) chamfered (i.e., angled from a longitudinal axis positioned through the hole) to aid in sliding the cup along the shaft of the manipulator tube. The proximal portion of the perimeter, on the other hand, can be straight and not chamfered/angled from the longitudinal axis to increase the retention force of the cup on the manipulator tube and to aid in preventing detachment of the cup from the manipulator tube. Other combinations of chamfering and not chamfering configurations are contemplated (as should be understood by a person of ordinary skill in the art in conjunction with a review of this disclosure). For example, the distal portion of the hole can be chamfered and the proximal portion can be straight/not angled, or each of the distal portion and the proximal portion can be partially chamfered (which may or may not be chamfered at an equal amount).

Other embodiments and implementations herein are directed to a device that includes a balloon that is tapered at its distal end (or angled away from the longitudinal axis) to sufficiently fit over a portion of a cup retention mechanism positioned on a proximal portion of the manipulator tube and to retain the balloon on the cup retention mechanism.

A particular non-limiting goal of utilization of the embodiments and implementations herein is to provide a device for manipulation of the uterus and injection of fluids or gases during laparoscopic procedures such as laparoscopic assisted vaginal hysterectomy (LAVH), total laparoscopic hysterectomy (TLH), minilap, laparoscopic tubal occlusion or diagnostic laparoscopy (and other similar procedures as should be understood by a person of ordinary skill in the art in conjunction with a review of this disclosure), and for the maintenance of a pneumoperitoneum by sealing the vagina during such procedures. In brief, the uterine manipulator device of an embodiment allows a medical practitioner to more easily access key surgical targets in the pelvic cavity by creating clear visibility of surgical landmarks and superior mobility of the uterus maximizing safe operative margins from the pelvic wall. The device can be structured and/or configured to displace the cervix away from the ureters, displace the bladder anetriorially, define the dissecting plane of a colpotomy, and prevent loss of pneumoperitoneum during the colpotomy (as noted above). Applicant has recognized and appreciated that it would be beneficial for medical practitioners to be able to approach such procedures with a higher degree of confidence in performing a consistent, predictable and repeatable procedure.

Generally, in one aspect, a uterine manipulator device includes: an elongated cannulated tube comprising a proximal end and a distal end; a cervical cup having a top proximal portion of a first diameter and a base distal portion of a second smaller diameter, wherein: the base distal portion includes a hole formed therein having a perimeter including a distal end and a proximal end, and including a longitudinal axis positioned therethrough; one of the proximal end of the perimeter and the distal end of the perimeter is angled away from the longitudinal axis and the other of the proximal end of the perimeter and the distal end of the perimeter is in line with the longitudinal axis; and the elongated cannulated tube is positioned through the hole in the cervical cup.

According to another aspect, a uterine manipulator device includes: an elongated cannulated tube comprising a proximal end and a distal end; a cervical cup having a top proximal portion of a first diameter and a base distal portion of a second smaller diameter, wherein: the base distal portion includes a hole formed therein having a perimeter including a distal end and a proximal end, and including a longitudinal axis positioned therethrough; the elongated cannulated tube is positioned through the hole in the cervical cup; a retention mechanism positioned on the elongated cannulated tube proximally to the cervical cup, wherein the retention mechanism is configured to prevent detachment of the cervical cup from the manipulator tube; and an intrauterine balloon positioned on the proximal end of the elongated cannulated tube and having a proximal end and a distal end, wherein the distal end of the intrauterine balloon is angled away from the longitudinal axis.

As used herein for purposes of the present disclosure, the terms "distal" and "proximal" are used to describe locations of embodiments of the device from the perspective of a patient.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

Figure 1:
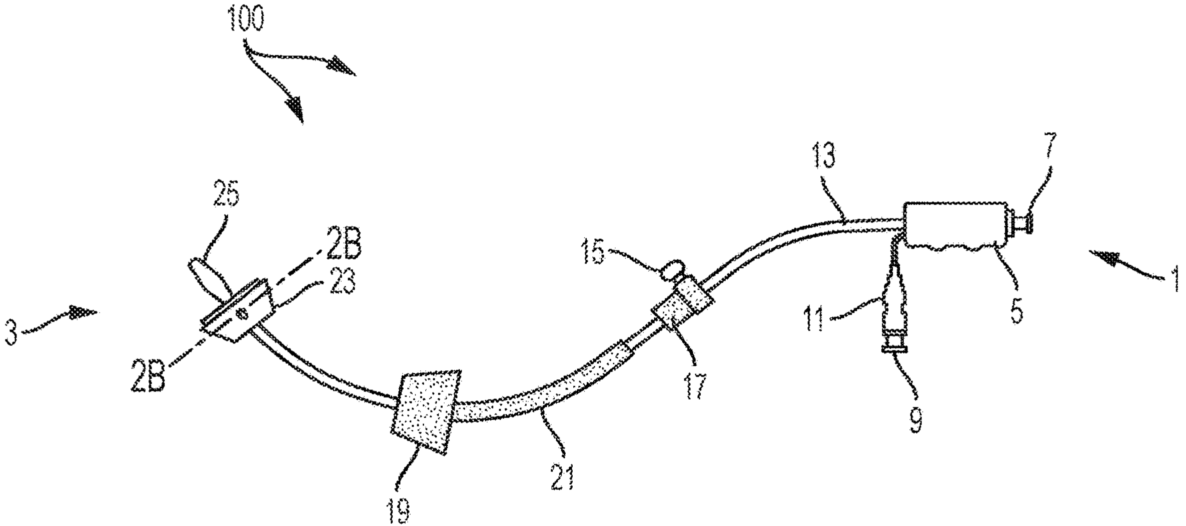
FIG. 1 is a schematic representation of a uterine manipulator device according to an embodiment.

Where applicable, like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION OF EMBODIMENTS

Referring to FIG. 1, in one embodiment, is a schematic representation of a uterine manipulator device 100. The uterine manipulator device 100 can include (from the distal end 1 to the proximal end 3) a handle 5, a dye injection port 7 positioned in the handle 5 (preferably through the distal end, and communicatively coupled to the intrauterine balloon 25), an inflation valve 9 (communicatively coupled to the intrauterine balloon 25), to which a syringe (e.g., 10 cc syringe, not shown) can be attached, and a pilot balloon 11 are attached to the handle 5 (preferably through the proximal end), and a cannulated manipulator tube 13. The cannulated manipulator tube 13 is curved at its proximal end and is straight at its distal end for easy introduction of the device 100, for manipulation of both retroverted and anteverted uteri, and for maintaining proper attitude of the uterus at the distal end. The cannulated manipulator tube 13 is connected to the handle 5 (preferably at the proximal end of the handle 5) and to the dye injection port 1, inflation valve 9, and pilot balloon 11 through the handle 5. The manipulator tube 13 is configured to anatomically conform to the angle of the sacral curve, and to allow for easy manipulation of the uterus. The manipulator tube 13 can be marked with reference graduations (not shown) from the proximal end 3. The graduations can be provided as a guide for comparison to a graduated uterine sound, and can aid in attaining proper depth of insertion during use. The handle 5, which can provide for the positioning of all four fingers on one side and the thumb on the opposite side (which can include a gripping/non-smooth surface such as a plurality of raised portions or other non-smooth surface structure as should be appreciated by a person of skill in the art in conjunction with a review of this disclosure), allows for easy manipulation of the uterus up, down and sideways.

The uterine manipulator device 100 incorporates a system of cup-like elevators positioned on the manipulator tube 13 (which is positioned through a hole formed at the base of each cup) to provide manipulation of the uterus, and retraction and elevation of the cervix. These cup-like elevators can include a vaginal cup 19 and a cervical cup 23. The vaginal cup 19 tapers from a top distal portion with a first diameter to a base proximal portion with a second smaller diameter and can include a cylindrical/tubular tail 21 positioned on the outside of the manipulator tube 13. A locking assembly is positioned distally to the tubular tail 21 and includes a cylindrical portion 17 and a thumbscrew 15. The cervical cup 23 is positioned on the proximal end of the manipulator tube 13, and can include sites/holes for suturing positioned through the side of the cervical cup 23. The cervical cup can include various volumes and diameters, examples of which are shown in Table 1 below:

TABLE 1

| Cervical Cup Volume | Cervical Cup Diameter | Cervical Cup Designation |
|---|---|---|
| 9.7 $cm^3$ (0.59 $in^3$) | 32 mm (1.26 in) | S |
| 14.3 $cm^3$ (0.87 $in^3$) | 34 mm (1.34 in) | M |
| 20.7 $cm^3$ (1.26 $in^3$) | 37 mm (1.46 in) | L |
| 26.7 $cm^3$ (1.63 $in^3$) | 40 mm (1.57 in) | XL |

An intrauterine balloon 25 is also shown, and is positioned on the most proximal portion of the manipulator tube 13. The balloon (e.g., 10 cc inflatable balloon) is configured and positioned to reduce the risk of uterine perforation and is used to stabilize the manipulator tube 13 within the uterine cavity 303 (see FIG. 4) during use.

Figure 2A:
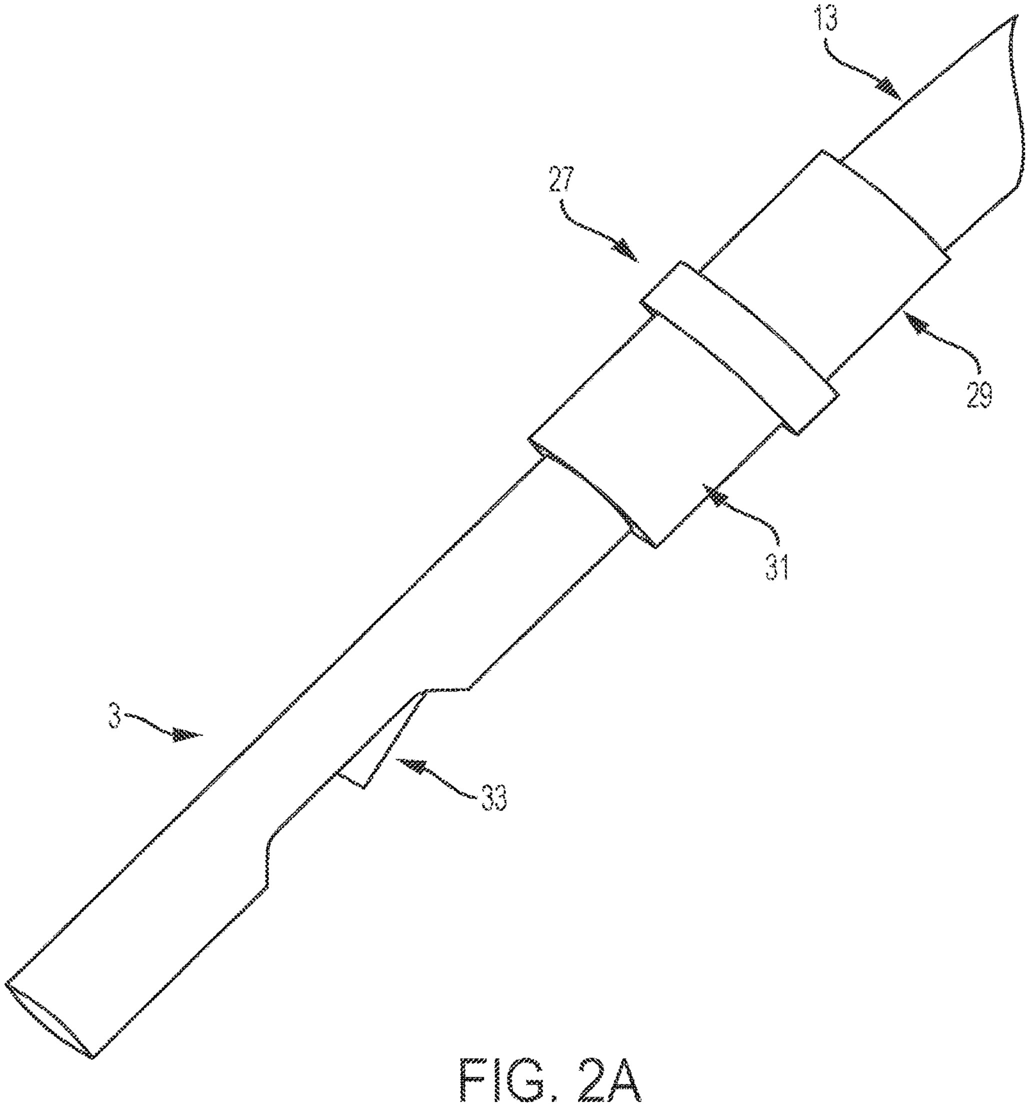
FIG. 2A is a schematic representation of the proximal end of the uterine manipulator device according to an embodiment.

Turning to FIG. 2A, in one embodiment, is a schematic representation of the proximal end 3 of the uterine manipulator device 100. The vaginal cup 19 and cervical cup 23 have been removed to show the retention mechanism for the cervical cup 23 positioned on the manipulator tube 13, which includes a retention ring 27 flanked by thermally fused heat shrink tubular portions 29 and 31 (which are configured to hold the retention ring in place on the manipulator tube 13). In brief, the retention ring 27, in conjunction with the heat shrink portions 29 and 31, is positioned on the manipulator tube 13 and configured to prevent detachment of the cervical cup 23 from the manipulator tube 13. The intrauterine balloon 25 has also been removed from FIG. 2, and the proximal portion of the manipulator tube 13 exposed by the removal of the intrauterine balloon 25 includes an opening with a proximal end of a tube 33 connected to the inflation valve 9 and pilot balloon 11 for inflating the intrauterine balloon 25, and to the dye injection port 7.

Figure 2B:
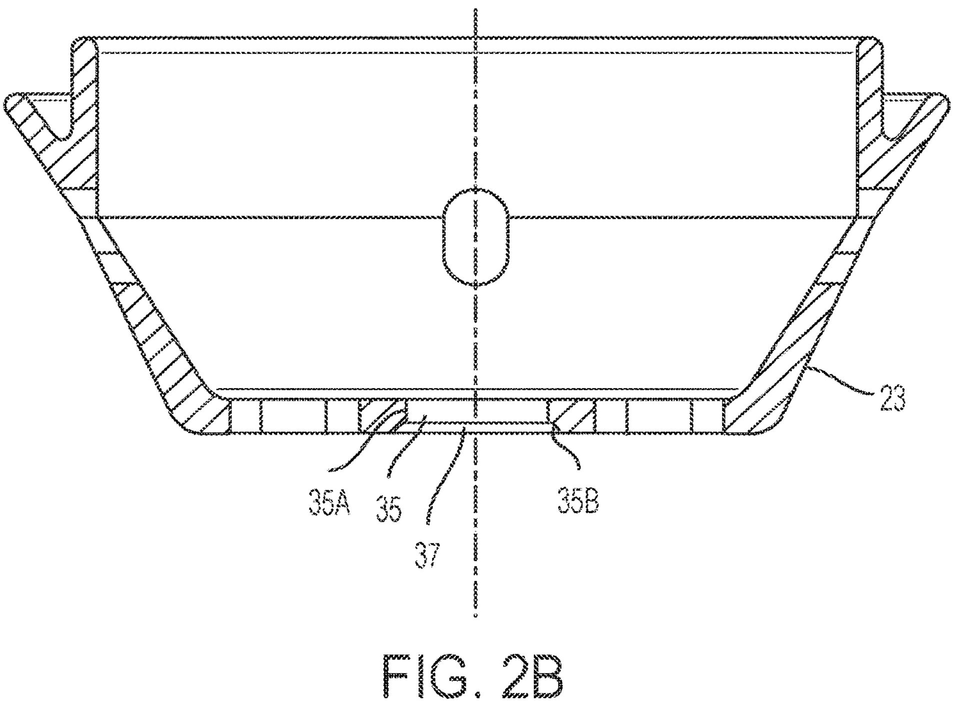
FIG. 2B is a schematic representation of the cervical cup of the uterine manipulator device taken along A-A of FIG. 1 according to an embodiment.
Figure 2C:
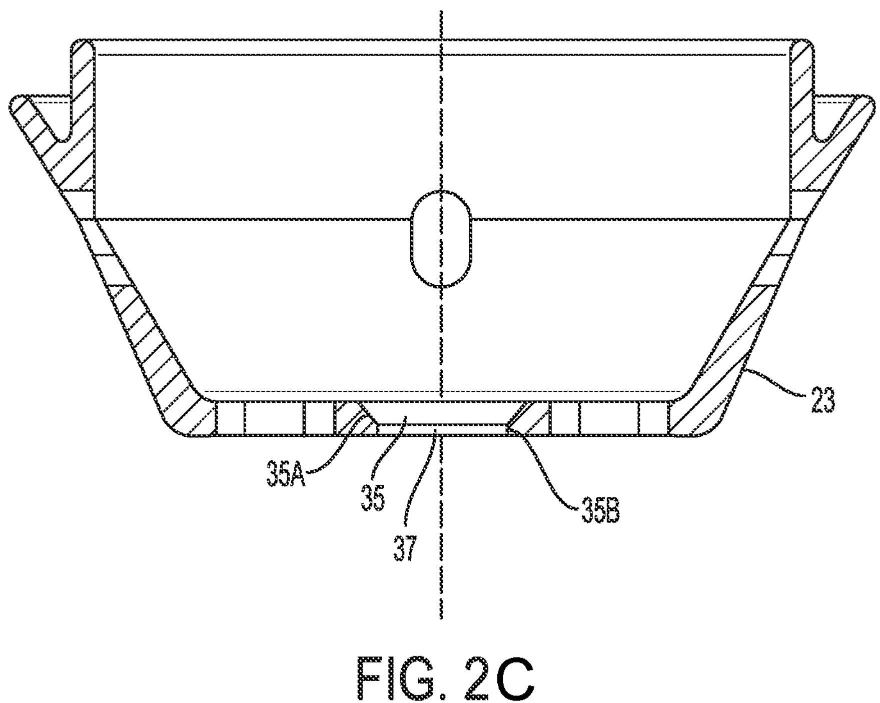
FIG. 2C is a schematic representation of the cervical cup of the uterine manipulator device taken along A-A of FIG. 1 according to an alternative embodiment.

Referring to FIG. 2B, in one embodiment, is a schematic representation of the cervical cup 23 taken along A-A of FIG. 1. As shown, the cervical cup 23 tapers from a top proximal portion with a first diameter to a base distal portion with a second smaller diameter including a central hole 37 having a perimeter 35. The perimeter is chamfered/angled away from the longitudinal axis A at the distal end 35B, and is straight/not angled with respect to the longitudinal axis A at the proximal end 35A. The chamfering of the perimeter aids in the movement of the cervical cup 23 along the manipulator tube 13. The straight/not angled perimeter portion aids in increasing the retention force of the cervical cup 23 on the manipulator tube 13 and in preventing detachment of the cup from the manipulator tube 13. Additionally, the hole 37 diameter was decreased (from 2.15 cm to 2.05 cm). The combination of the straight/not angled perimeter portion and the narrowing of the diameter of the hole 37 significantly increased the retention force of the cervical cup 23 on the manipulator tube 13. In another embodiment, as shown in FIG. 2C, a configuration opposite FIG. 2B is depicted where end 35A is angled away and end 35B is straight with respect to the longitudinal axis A to aid in the movement of the cervical cup 23 along the manipulator tube 13.

Figure 3A:
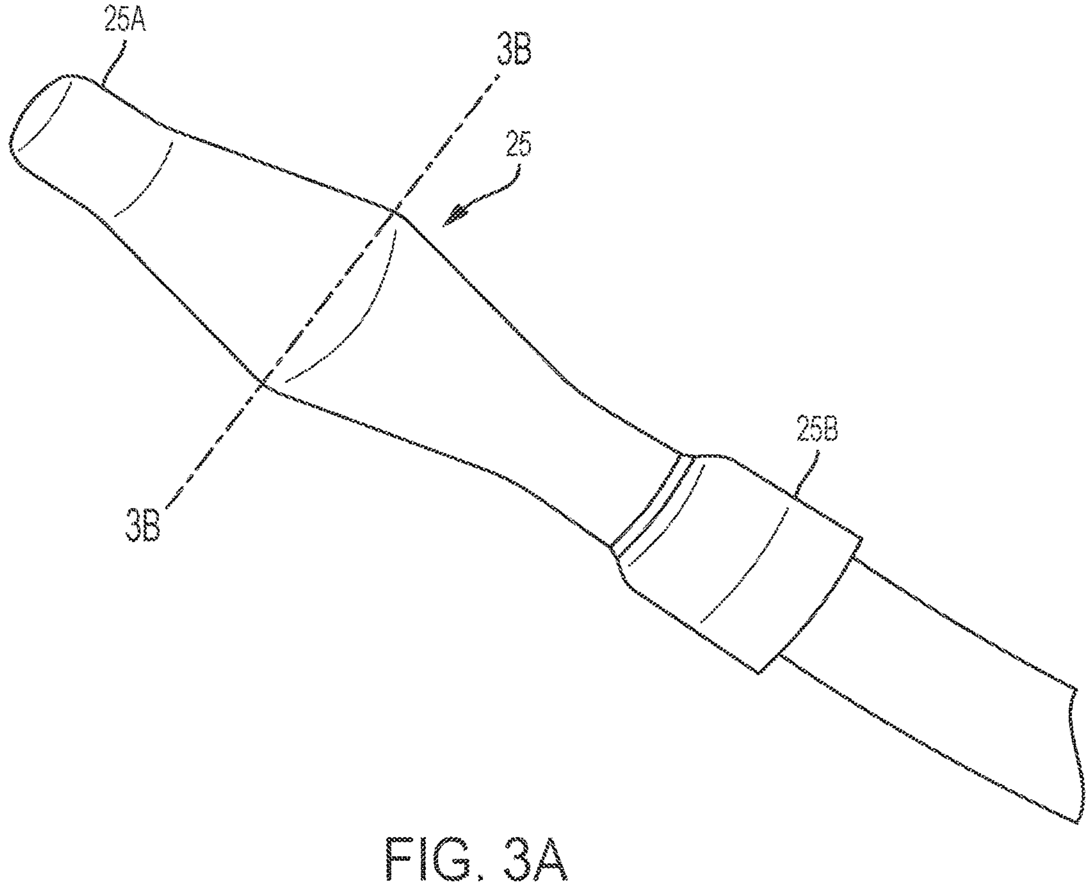
FIG. 3A is a schematic representation of the proximal end of the uterine manipulator device according to an embodiment.

Turning to FIG. 3A, in one embodiment, is a schematic representation of the proximal end 3 of the uterine manipulator device 100. The vaginal cup 19 and cervical cup 23 have been removed. The intrauterine balloon 25 is shown with a proximal end 25A positioned over the proximal end 3 of the device 100, and a distal end 25B positioned over the retention mechanism.

Figure 3B:
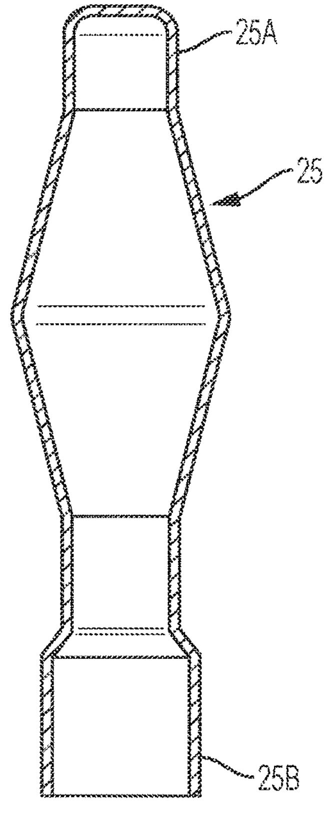
FIG. 3B is a schematic representation of the intrauterine balloon of the uterine manipulator device taken along A-A of FIG. 3A according to an embodiment.

Referring to FIG. 3B, in one embodiment, is a schematic representation of the intrauterine balloon 25 taken along A-A of FIG. 3A. As shown, the distal end 25B of the intrauterine balloon 25 is angled a certain amount (e.g., three degrees total) from the longitudinal axis to sufficiently fit over a portion of the retention mechanism and to retain the intrauterine balloon 25 on the cup retention mechanism. Such a structure and configuration of the distal end 25B of the intrauterine balloon 25 assists with a proper and clean assembly (no "bunching") of the intrauterine balloon 25 on the device 100.

Figure 4:
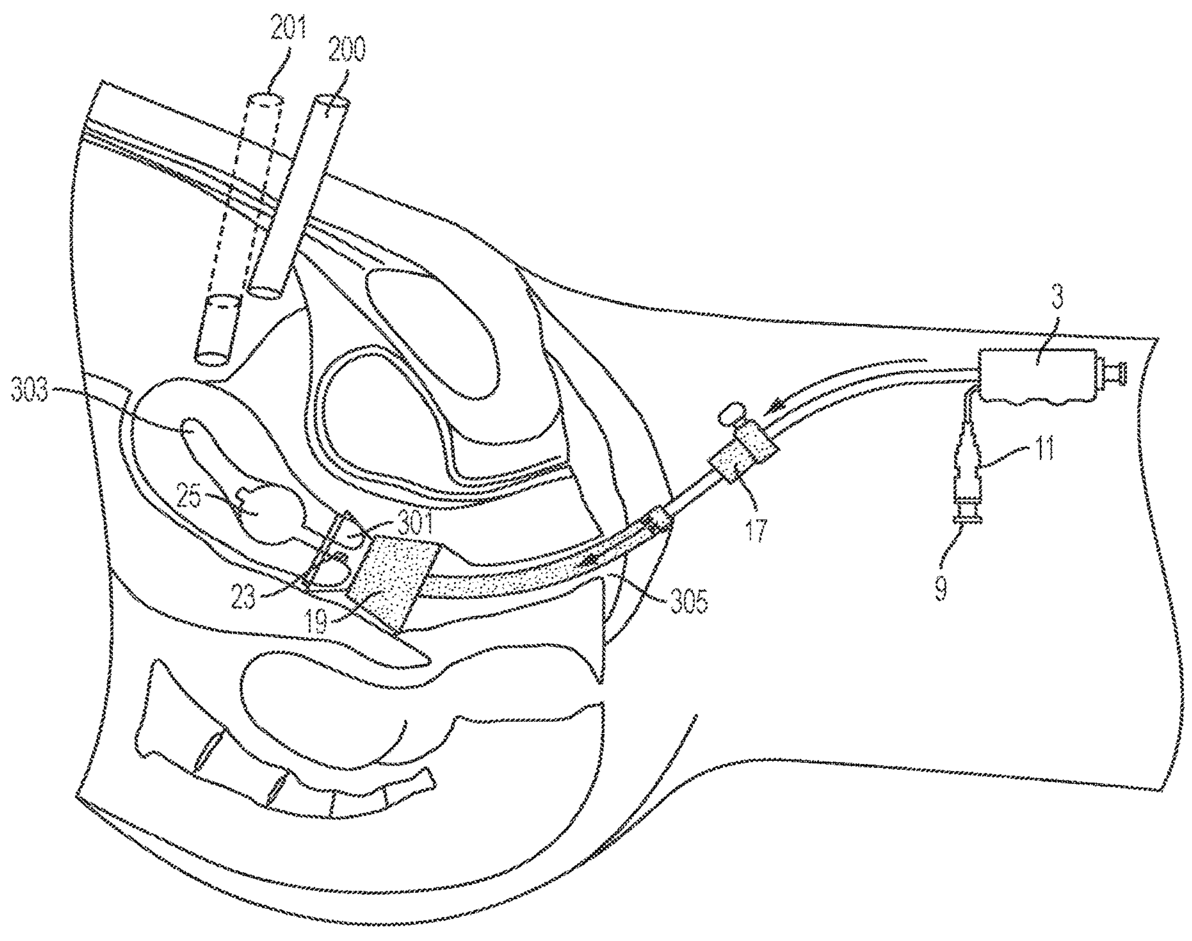
FIG. 4 is a schematic representation of the use of the uterine manipulator device according to an embodiment.

Referring to FIG. 4, in one embodiment, is a schematic representation of the use of the uterine manipulator device 100. The uterine manipulator device 100 is shown positioned through the vagina 305 with the intrauterine balloon 25 in the uterine cavity 303 and the vaginal fornix 301 positioned within the cervical cup 23. After the intrauterine balloon 25 is positioned within the uterine cavity 303, a syringe is attached to the inflation valve 9 to inflate the intrauterine balloon 25 (with, e.g. 7 cc of air and up to, e.g., 10 cc of air). The syringe is then removed to prevent spontaneous deflation of the intrauterine balloon 25 by backward pressure. The cervical cup 23 is then slid proximally along the manipulator tube 13 until its outer edges surround the vaginal fornix 301 (as shown). The cervical cup 23 can optionally be sutured in place. The vaginal cup 19 is then slid proximally along the manipulator tube 13 until it meets the distal edge of the cervical cup 23 and is completely seated against the vaginal 305 walls and is configured, structured and/or positioned to ensure maintenance of pneumoperitoneum as needed. The locking assembly is slid proximally to meet the cylindrical/tubular tail 21 of the vaginal cup 19 and secured in place by turning the thumbscrew until it is tight. Manipulation of the uterus can then be carried out as may be necessary based on the particular procedure (as should be understood by a person of ordinary skill in the art in conjunction with a review of this disclosure), and various devices including visualization and other surgical devices (200, 201) can be inserted through incisions made in the abdomen of the patient.

While embodiments of the present invention has been particularly shown and described with reference to certain exemplary 8 embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A method of using a uterine manipulator device, comprising:

providing a uterine manipulator device, comprising:

an elongated cannulated tube comprising a proximal end and a distal end;

a cervical cup having a top proximal portion of a first diameter and a base distal portion of a second smaller diameter, wherein:

the base distal portion includes a hole formed therein having a perimeter including a distal end and a proximal end, and including a longitudinal axis positioned therethrough;

one of the proximal end of the perimeter and the distal end of the perimeter is angled away from the longitudinal axis and the other of the proximal end of the perimeter and the distal end of the perimeter is in line with the longitudinal axis;

the elongated cannulated tube is positioned through the hole in the cervical cup; and an intrauterine balloon positioned on the proximal end of the elongated cannulated tube and having a wall and including a proximal end and a distal end, wherein a distal most end of the intrauterine balloon includes an opening, wherein a distal portion of the distal end of the intrauterine balloon wall includes a first portion having a length that is angled in an outward direction away from the longitudinal axis and a second portion distal to the first portion, the second portion having a length that is parallel to the longitudinal axis, wherein the first and second portions collectively extend in a direction and position from a proximal portion of the distal end to the distal most end of the intrauterine balloon at the opening;

positioning the uterine manipulator device in position; and inflating the intrauterine balloon.

2. The method of claim 1, wherein the proximal end of the elongated cannulated tube of the uterine manipulator device is nonlinear.

3. The method of claim 1, wherein the uterine manipulator device further comprises a vaginal cup positioned distally from the cervical cup on the elongated cannulated tube, wherein the vaginal cup includes a top distal portion with a first diameter and a base proximal portion with a second smaller diameter, and wherein the vaginal cup is configured to maintain pneumoperitoneum during use.

4. The method of claim 3, wherein the uterine manipulator device further comprises a locking assembly positioned distally from the vaginal cup configured to lock the cervical cup and the vaginal cup in place during use.

5. The method of claim 1, wherein the uterine manipulator device further comprises a retention mechanism comprising a retention ring positioned on the elongated cannulated tube proximally to the cervical cup, wherein the retention ring is configured to prevent detachment of the cervical cup from the elongated cannulated tube.

6. The method of claim 5, wherein the retention mechanism of the uterine manipulator device further comprises a ring of heat shrink positioned on the elongated cannulated tube adjacent to the retention ring.

7. The method of claim 1, wherein the uterine manipulator device further comprises a handle positioned on the distal end of the elongated cannulated tube.

8. The method of claim 7, wherein the uterine manipulator device further comprises an inflation valve positioned through the handle and communicatively coupled to the intrauterine balloon.

9. The method of claim 7, wherein the uterine manipulator device further comprises a dye injection port positioned through the handle and communicatively coupled to the intrauterine balloon.

10. A method of using a uterine manipulator device, comprising:

providing a uterine manipulator device, comprising:

an elongated cannulated tube comprising a proximal end and a distal end;

a cervical cup having a top proximal portion of a first diameter and a base distal portion of a second smaller diameter, wherein:

the base distal portion includes a hole formed therein having a perimeter including a distal end and a proximal end, and including a longitudinal axis positioned therethrough;

the elongated cannulated tube is positioned through the hole in the cervical cup;

a retention mechanism positioned on the elongated cannulated tube proximally to the cervical cup, wherein the retention mechanism is configured to prevent detachment of the cervical cup from the elongated cannulated tube; and an intrauterine balloon positioned on the proximal end of the elongated cannulated tube and having a wall and including a proximal end and a distal end, wherein a distal most end of the intrauterine balloon includes an opening, wherein a distal portion of the distal end of the intrauterine balloon wall includes a first portion having a length that is angled in an outward direction away from the longitudinal axis and a second portion distal to the first portion, the second portion having a length that is parallel to the longitudinal axis, wherein the first and second portions collectively extend in a direction and position from a proximal portion of the distal end to the distal most end of the intrauterine balloon at the opening;

positioning the uterine manipulator device in position; and inflating the intrauterine balloon.

11. The method of claim 10, wherein the proximal end of the elongated cannulated tube of the uterine manipulator device is nonlinear.

12. The method of claim 11, wherein the uterine manipulator device further comprises a vaginal cup positioned distally from the cervical cup on the elongated cannulated tube, wherein the vaginal cup includes a top distal portion with a first diameter and a base proximal portion with a second smaller diameter, and wherein the vaginal cup is configured to maintain pneumoperitoneum during use.

13. The method of claim 12, wherein the uterine manipulator device further comprises a locking assembly positioned distally from the vaginal cup configured to lock the cervical cup and the vaginal cup in place during use.

14. The method of claim 10, wherein the retention mechanism further comprises a retention ring positioned on the elongated cannulated tube proximally to the cervical cup, wherein the retention ring is configured to prevent detachment of the cervical cup from the elongated cannulated tube.

15. The method of claim 14, wherein the retention mechanism of the uterine manipulator device further comprises a ring of heat shrink positioned on the elongated cannulated tube adjacent to the retention ring.

16. The method of claim 10, wherein the uterine manipulator device further comprises a handle positioned on the distal end of the elongated cannulated tube.

17. The method of claim 16, wherein the uterine manipulator device further comprises an inflation valve positioned through the handle and communicatively coupled to the intrauterine balloon.

18. The method of claim 16, wherein the uterine manipulator device further comprises a dye injection port positioned through the handle and communicatively coupled to the intrauterine balloon.

* * * * *